US007469769B1

(12) United States Patent
Hmayakyan et al.

(10) Patent No.: US 7,469,769 B1
(45) Date of Patent: Dec. 30, 2008

(54) STETHOSCOPE COVER AND DISPENSER THEREFOR

(76) Inventors: Samvel Hmayakyan, 607 N. Central Ave., Glendale, CA (US) 91203; Vahen Joakim, 659 W. Dryden St., Glendale, CA (US) 91202

( * ) Notice: Subject to any disclaimer, the term of this patent is extended or adjusted under 35 U.S.C. 154(b) by 0 days.

(21) Appl. No.: 11/999,556

(22) Filed: Dec. 5, 2007

(51) Int. Cl.
  *A61B 7/02* (2006.01)
  *B65G 59/06* (2006.01)
(52) U.S. Cl. ............................ 181/131; 221/176
(58) Field of Classification Search ............... 181/131, 181/130, 129; 600/528; 381/67; 221/266, 221/176, 263; 379/452, 439
See application file for complete search history.

(56) References Cited

U.S. PATENT DOCUMENTS

| | | | | | |
|---|---|---|---|---|---|
| 1,472,530 | A | * | 10/1923 | McComas | 379/447 |
| 3,169,171 | A | * | 2/1965 | Wachs et al. | 379/452 |
| 3,929,254 | A | | 12/1975 | Artze | |
| 4,867,268 | A | * | 9/1989 | Ulert | 181/137 |
| 4,871,046 | A | * | 10/1989 | Turner | 181/131 |
| 4,876,715 | A | * | 10/1989 | Neubert | 379/452 |
| 5,428,193 | A | * | 6/1995 | Mandiberg | 181/131 |
| 5,448,025 | A | * | 9/1995 | Stark et al. | 181/131 |
| 5,466,897 | A | | 11/1995 | Ross et al. | |
| 5,686,706 | A | * | 11/1997 | Wurzburger | 181/131 |
| 5,808,244 | A | * | 9/1998 | Knight et al. | 181/131 |
| 6,041,889 | A | | 3/2000 | Stark et al. | |
| 6,206,134 | B1 | | 3/2001 | Stark et al. | |
| 6,467,568 | B1 | * | 10/2002 | Kemper | 181/131 |
| 6,499,560 | B1 | * | 12/2002 | Lang et al. | 181/131 |
| 6,520,281 | B1 | * | 2/2003 | Deslauriers et al. | 181/131 |
| 6,575,917 | B2 | * | 6/2003 | Giroux et al. | 600/528 |
| 6,643,998 | B1 | * | 11/2003 | Curtis et al. | 53/594 |
| 7,117,971 | B1 | * | 10/2006 | Cornacchia | 181/131 |
| 7,282,186 | B2 | * | 10/2007 | Lake et al. | 422/300 |
| 2007/0045039 | A1 | * | 3/2007 | Agahi et al. | 181/131 |

* cited by examiner

*Primary Examiner*—Edgardo San Martin

(57) ABSTRACT

A protective cover for a stethoscope head and an apparatus for quickly and easily interconnecting the protective cover with the stethoscope head. The apparatus includes a cover-positioning device that positions the protective cover so that it can be quickly and easily interconnected with the stethoscope head. The cover positioning device includes a base having a planar portion and an upstanding rim connected to the planar portion, the upstanding rim defining an opening for receiving the stethoscope head therethrough. Following examination of the patient using the stethoscope with the protective head covering, the protective covering can be quickly and easily removed from the stethoscope head and suitably disposed of so as to prevent skin bacteria and like contaminants that may have contaminated the protective cover during patient examination from undesirably being transmitted to the next patient.

10 Claims, 4 Drawing Sheets

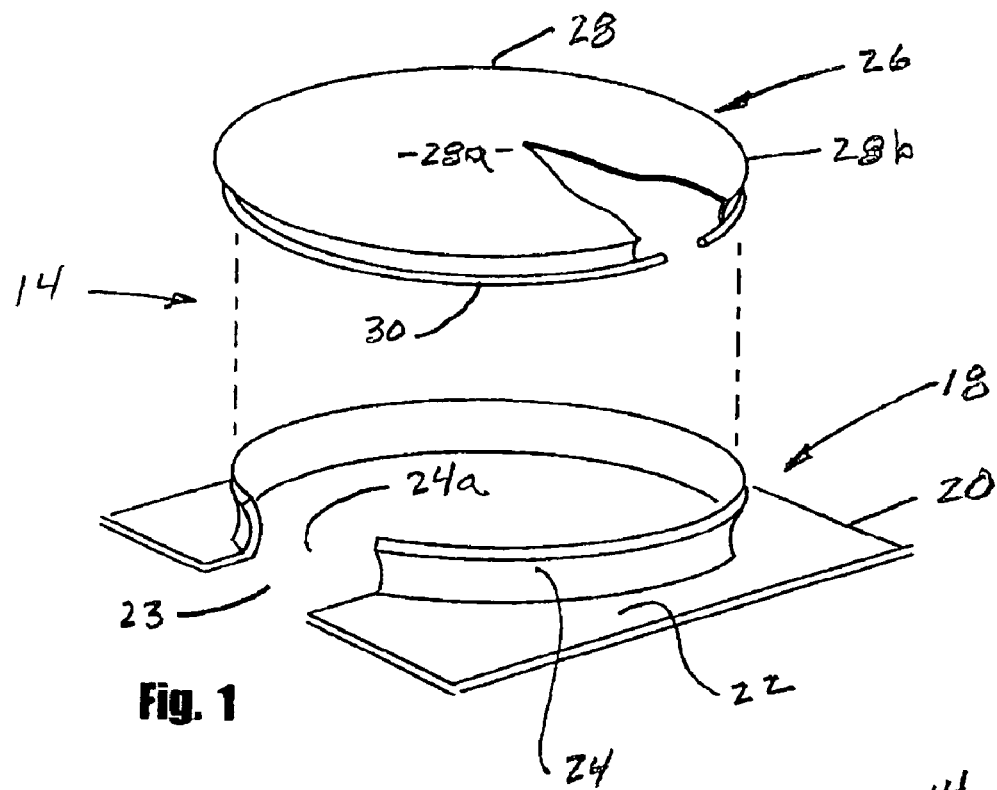
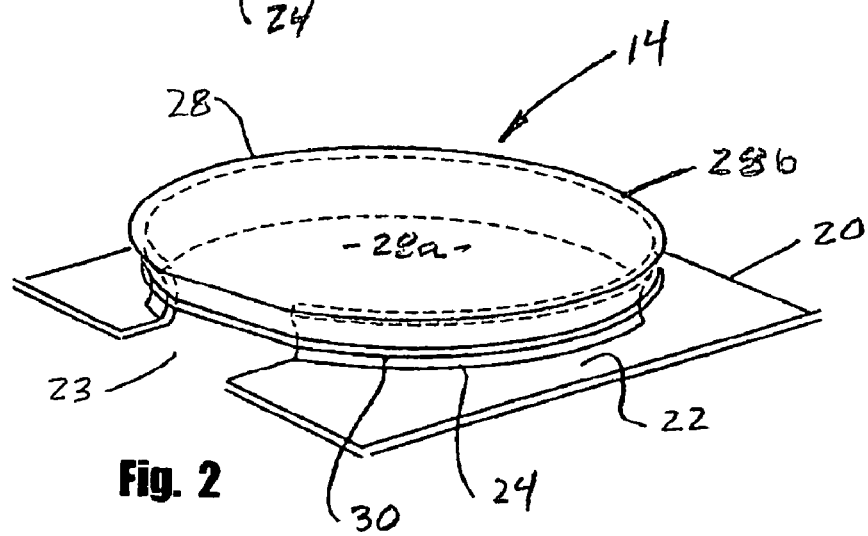

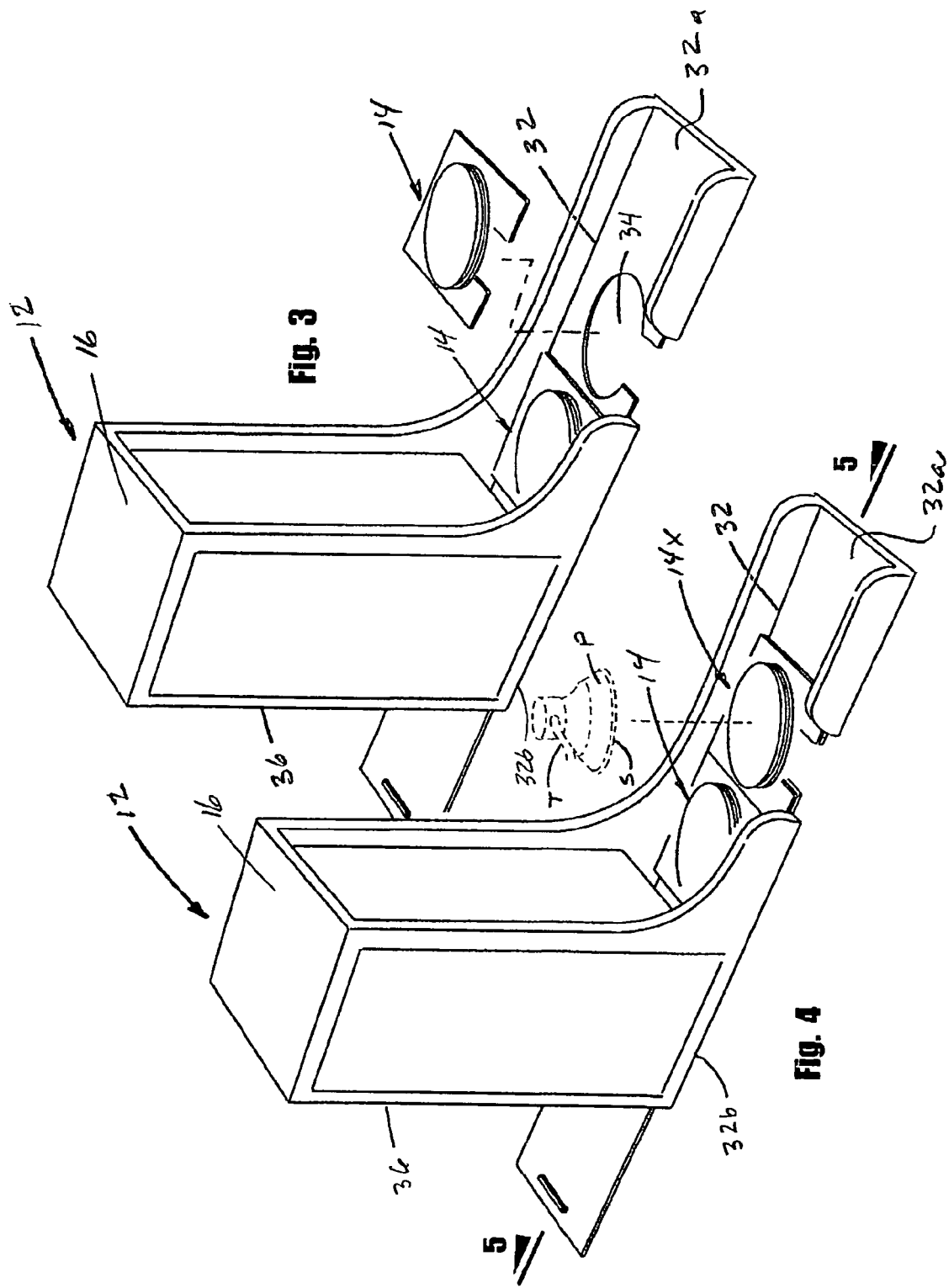

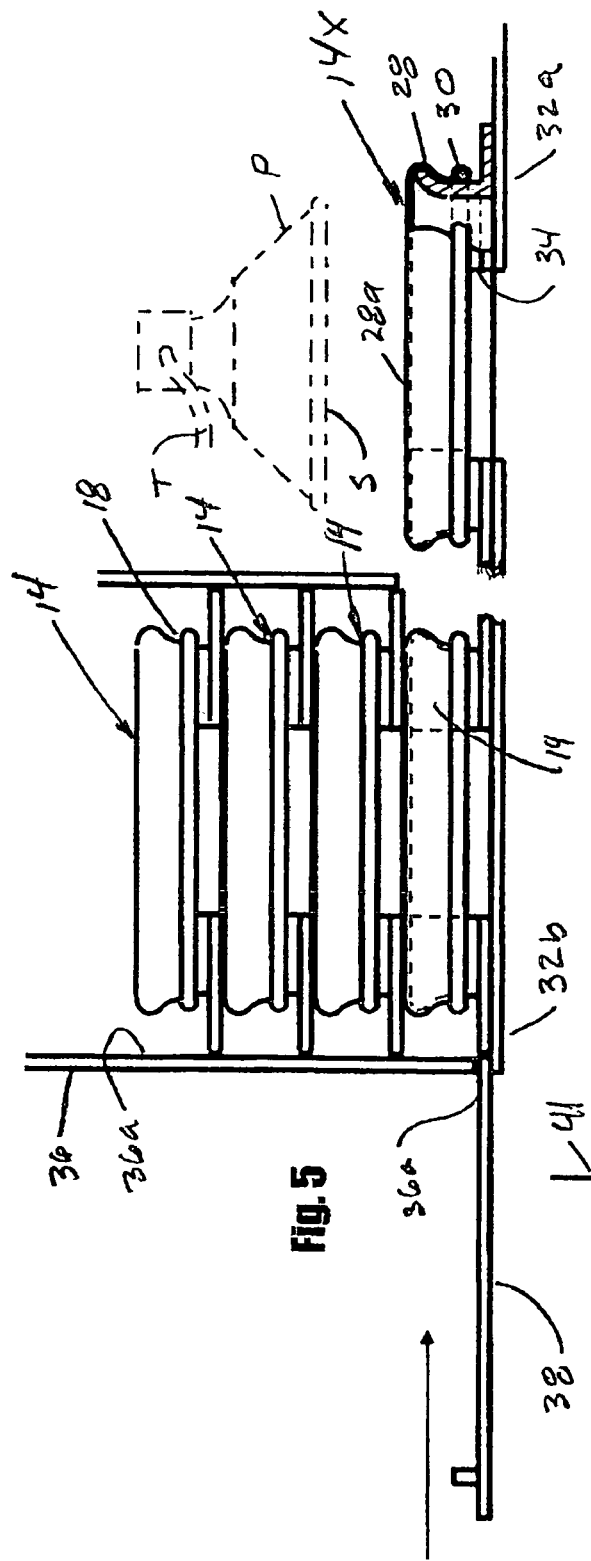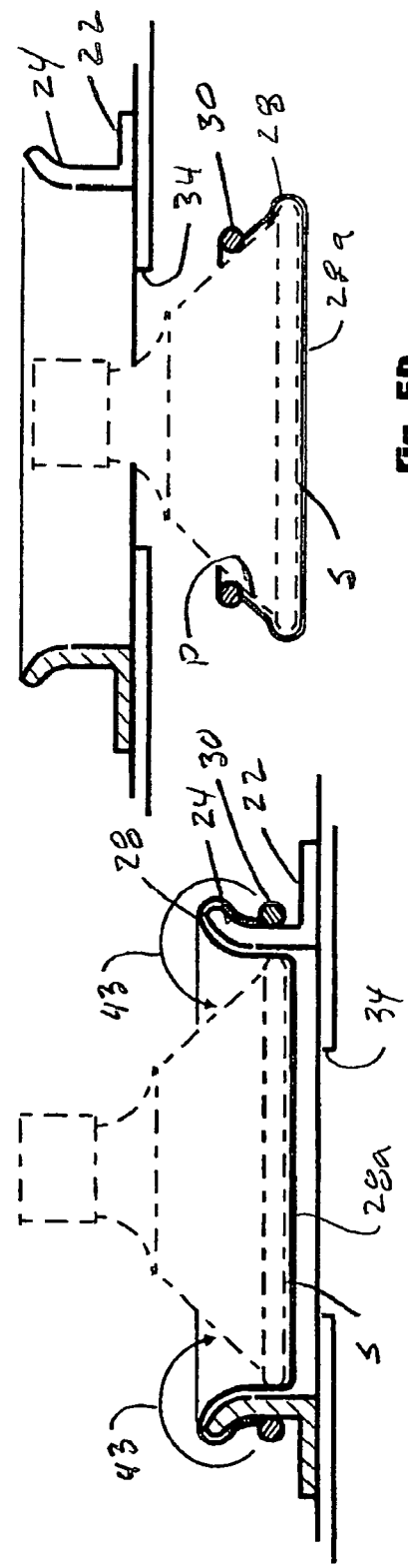

STETHOSCOPE COVER AND DISPENSER THEREFOR

BACKGROUND OF THE INVENTION

1. Field of the Invention

The present invention relates generally to medical devices. More particularly, the invention concerns a disposable cover for a stethoscope head and an apparatus for dispensing the disposable cover.

2. Discussion of the Prior Art

A stethoscope is an acoustic medical device for auscultation, or listening, to internal sounds in a human or animal body. It is most often used to listen to heart sounds and breathing (breath sounds), though it is also used to listen to intestines and blood flow in arteries and veins. The stethoscope operates on the transmission of sound from the chest piece, via air-filled hollow tubes, to the listener's ears. The chest piece can be placed against the patient for sensing relatively high frequency sound via a diaphragm which is usually provided in the form of a plastic disc. If the diaphragm is placed on the patient, body sounds vibrate the diaphragm creating acoustic pressure waves which travel up the tubing to the listener's ears. In use, the stethoscope is typically applied to the skin of the neck, chest, or back portions of the patient and often becomes contaminated with skin bacteria and like contaminants that can undesirably be transmitted to the next patient unless the portions of the stethoscope that come in contact with a patient are sterilized after each use. The transmission of bacterial infections among patients, particularly in a hospital setting, has been aggravated by the development of antibiotic-resistant strains of staphylococcal infections. It is this problem that the apparatus of the present invention seeks to overcome by providing a novel stethoscope cover and a dispensing apparatus for quickly and easily dispensing the stethoscope cover.

A number of different types of stethoscope covers and apparatus for dispensing the covers have been suggested in the past. Exemplary of such prior art is the stethoscope cover and dispensing apparatus disclosed in U.S. Pat. No. 6,206,134 issued to Stark, et al. The Stark, et al., patent discloses a stethoscope head cover which overlies the diaphragm of the stethoscope and the surrounding rim thereof and which is fabricated from a thin sheet of plastic with a discontinuous layer of peelable adhesive on one surface of the plastic. The discontinuous layer of adhesive is in a predetermined pattern and the pattern is selected so that air passageways are provided from the regions between the cover and the diaphragm and past the rim to regions external the stethoscope. The cover generally comprises a flat, thin plastic sheet with the discontinuous layer of a peelable adhesive applied to one surface of the sheet. The adhesive adheres to both the diaphragm and the rim of the stethoscope leaving the aforesaid air passages for eliminating trapped air pockets or bubbles between the diaphragm and the cover.

U.S. Pat. No. 6,019,187 issued to Appavu discloses a disposable stethoscope cover diaphragm that is removably attached over the outer edge of a stethoscope high frequency pickup in order to isolate the pickup from pathogens contacted when the stethoscope is used to examine a person. The cover diaphragm can be used as the diaphragm of a stethoscope pickup and can be used with a diaphragm supplied with the stethoscope. After the cover diaphragm has been used it can be discarded and destroyed or, alternatively, can be cleaned for reuse.

U.S. Pat. No. 5,466,897 issued to Ross, et al., discloses a dispenser for use in dispensing disposable stethoscope diaphragms for removable attachment to a stethoscope head, where the diaphragms are supplied in a stacked array in a tube. The diaphragms are dispensed by a plate slidably mounted on the base for movement between retracted and extended positions. A cradle formed in the plate receives a single diaphragm through the opening when the dispensing plate is in its retracted position. Movement of the dispensing plate from its retracted to extended position is effective to place a diaphragm in the plate cradle in a position that allows the diaphragm to be attached to a stethoscope head by pressing the stethoscope head against the diaphragm.

SUMMARY OF THE INVENTION

By way of brief summary, one form of the present invention comprises a handheld cover dispensing unit that can be used to interconnect a disposable stethoscope cover with a conventional stethoscope head. The cover dispensing unit includes, in combination, a cover positioning device and a disposable stethoscope cover for removable attachment to a stethoscope head. The cover-positioning device comprises a base having a planar portion and an upstanding rim connected to the planar portion, the upstanding rim defining an opening for receiving the stethoscope head therethrough. The disposable stethoscope cover comprises a thin, yieldably deformable membrane-like central portion having a peripheral portion and an elastomeric bead interconnected with the peripheral portion, the elastomeric bead being removably receivable over said upstanding rim of the cover-positioning device.

Another form of the present invention comprises a wall, or desktop mounted stethoscope head covering apparatus for dispensing a plurality of cover dispensing units of the character described in the preceding paragraph. This form of the invention includes a novel feed unit for sequentially dispensing the cover dispensing units. The feed unit includes a housing having a base having a forward portion and a rearward portion and an upstanding tower connected to the rearward portion of the base for holding a plurality of stacked cover dispensing units. An ejector slide is operably associated with the upstanding tower for moving a selected one of the cover dispensing units from the upstanding tower to a position over a generally key-hole-shaped opening formed in said base of said feed unit so that the disposable cover can be conveniently interconnected with the stethoscope head.

With the forgoing in mind, it is an object of the invention to provide a novel handheld cover dispensing unit that can be used to quickly and easily interconnect a disposable, protective stethoscope cover with a stethoscope head.

Another object of the invention is to provide a cover dispensing unit of the aforementioned character in which the protective stethoscope cover includes a thin, membrane-like central portion that is positioned in close protective engagement with the lower surface of the stethoscope head when the cover is interconnected with the stethoscope head.

Another object of the invention is to provide a protective stethoscope head cover of the character described in the preceding paragraph that can be quickly and easily removed from the stethoscope head following examination of the patient and then suitably disposed of so as to prevent skin bacteria and like contaminants that may have contaminated the protective cover during patient examination from undesirably being transmitted to the next patient.

Another object of the invention is to provide a hand-held dispensing unit of type described that is of simple compact construction and one that can be inexpensively manufactured in quantity.

Another object of the invention is to provide a novel wall or desk mounted feed unit that can be used to conveniently feed dispensing units of the character described from an upstanding tower containing a plurality of cover dispensing and sequentially position them on a strategically designed base so that the protective cover of the dispensing unit can be removed from the cover positioning device and quickly and easily interconnected with a stethoscope head.

These and other objectives of the invention will be met by the novel apparatus of the invention, the character of which is described in the paragraphs that follow.

BRIEF DESCRIPTION OF THE DRAWINGS

FIG. 1 is a generally perspective, exploded view of one form of the cover position devices of the invention for positioning a disposable stethoscope head cover in the manner such that the cover can be conveniently interconnected with a stethoscope head.

FIG. 2 is a generally perspective view, similar to FIG. 1, showing the disposable stethoscope head cover interconnected with the cover-positioning device to form the cover dispenser unit of the invention.

FIG. 3 is a generally perspective, exploded view of one form of the feed unit of the invention for sequentially dispensing the cover dispensing units.

FIG. 4 is a generally perspective view, similar to FIG. 3, illustrating the manner in which the cover dispensing units are sequentially dispensed from the tower of the feed unit.

FIG. 5 is a greatly enlarged, fragmentary, foreshortened, cross-sectional, side-elevational view illustrating the manner in which the cover dispensing units of the invention are stacked within the tower of the feed unit and are strategically positioned on the base of the feed unit for interconnection of the disposable cover with a stethoscope head of the general character illustrated in the phantom lines in FIG. 5.

FIG. 5A is a fragmentary view, similar to the right-hand portion of FIG. 5, illustrating the manner in which the stethoscope head, shown in phantom lines, is mated with the cover-positioning device.

FIG. 5B is a fragmentary view, similar to FIG. 5A, illustrating the disposable cover having been interconnected with the stethoscope head which is here shown in phantom lines.

DESCRIPTION OF THE INVENTION

Figure 5C:
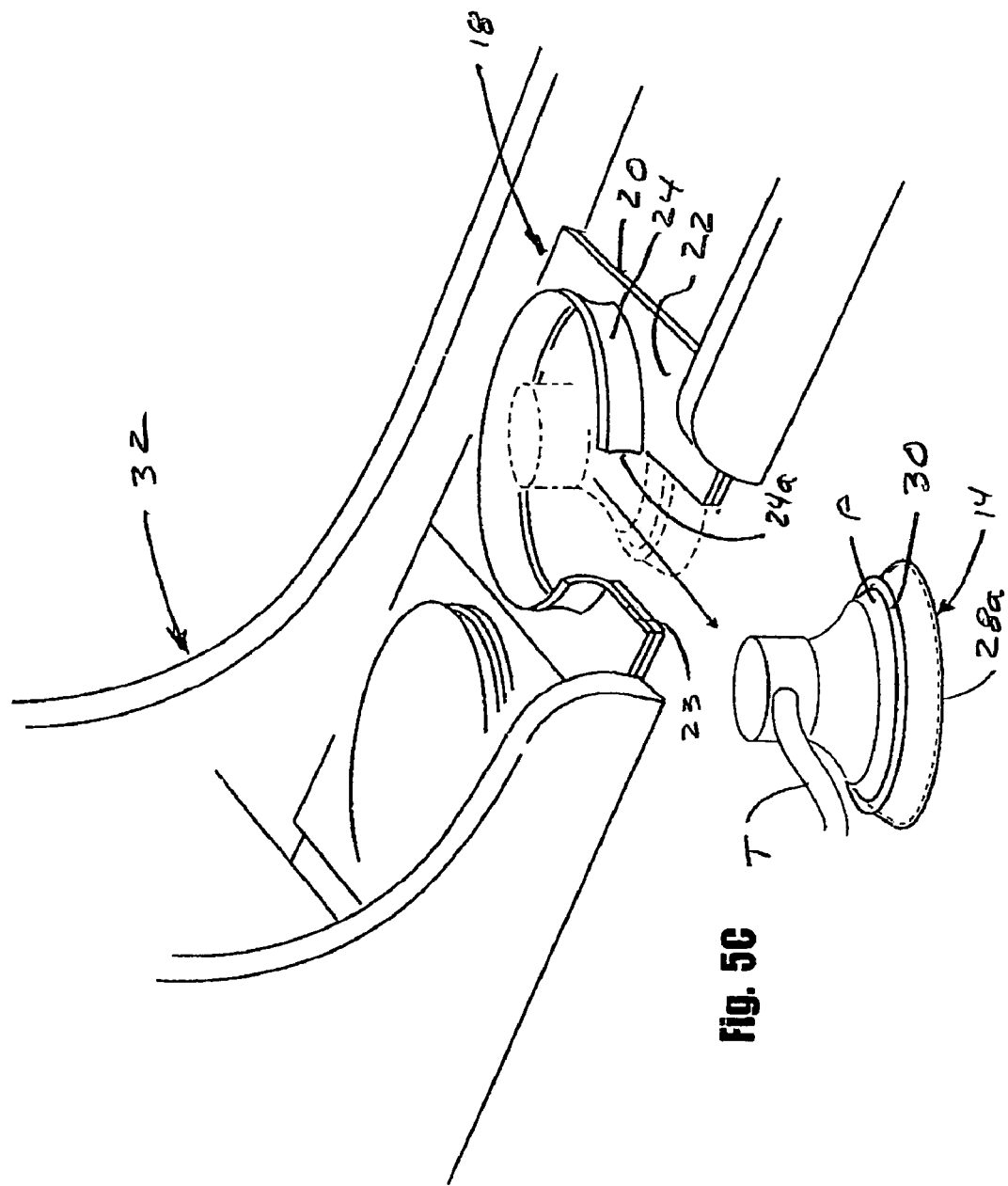
FIG. 5C is a generally illustrative view showing removal from the feed unit of the assemblage made up of the stethoscope head and the protective cover.

Referring to the drawings and particularly to FIGS. 3 and 4, one form of the stethoscope head covering apparatus of the present invention is there shown and generally designated by the numeral 12. Apparatus 12 here comprises a plurality of cover dispensing units 14 of the character illustrated in FIG. 2 of the drawings and a feed unit 16 of the character shown in FIGS. 3 and 4 of the drawings. In a manner presently to be described, feed unit 16 functions to sequentially dispense the plurality of cover dispensing units 14. However, it is to be understood that, as previously described, the cover dispensing units 14 can be packaged and distributed as individual handheld units that can be used by the physician to interconnect the protective cover with the stethoscope head.

As best seen in FIGS. 1 and 2 of the drawings, each cover dispensing unit 14 comprises a positioning device 18 that includes a base 20 having a generally planar portion 22 and an upstanding rim 24 that is connected to portion 22 in the manner shown in FIG. 1. For a purpose presently to be described, generally planar portion 22 of the base is provided with an open segment 23. Similarly, upstanding rim 24 is provided with an open segment 24a that is disposed in alignment with open segment 23 of the planar portion of the base.

Connected to each of the cover-positioning devices 18 to form a dispensing unit 14 (see FIG. 2) is a cover assembly 26 that comprises a uniquely constructed disposable cover 28. As best seen in FIG. 1 disposable cover 28 has a thin, yieldably deformable, membrane-like central portion 28a and a peripheral portion 28b. Connected to peripheral portion 28b is an elastomeric bead 30 that is removably receivable over the upstanding rim 24 of the base 20 in the manner shown in FIG. 2 of the drawings.

Considering once again the dispenser unit 16 of the apparatus of the invention, as illustrated in FIGS. 3 and 4 of the drawings, dispenser unit 16 here comprises a base 32 having a forward portion 32a and a rearward portion 32b. As indicated in FIG. 3 of the drawings, forward portion 32a is provided with a generally key-hole-shaped opening 34 the purpose of which will presently be described.

Connected to the rearward portion 32b of base 32 is an upstanding dispensing tower 36 having an interior chamber 36a (FIG. 5) that, in the manner shown in FIG. 5, functions to hold a plurality of stacked cover dispensing units 14. For a purpose presently to be described, the chamber is provided with a slot 36a that is formed proximate the rearward portion 32b of the base (see FIG. 5). Slidably receivable within slot 36a for movement between a first retracted position and a second dispensing position is an ejector slide 38. When the selector slide has been moved from its first retracted position and to its second dispensing position, a selected one of the cover dispensing units 14, such as the device identified in FIGS. 3 and 4 by the numeral 14x, has been moved along the base 32 from the inward position shown in FIG. 3 into the outward position shown in FIGS. 4 and 5 wherein it resides over the generally key-hole-shaped opening 34.

With the cover dispensing units designated as 14x in position over the generally key-hole-shaped opening 34 (FIG. 5), the disposable cover assembly 26 can be interconnected with the stethoscope head in the manner illustrated in FIGS. 5, 5A and 5B of the drawings. More particularly, in order to interconnect the disposable cover with the stethoscope head, the stethoscope head is moved in the direction of the arrow 41 of FIG. 5A from the position shown in the phantom lines in FIG. 5 into the downward position shown by the phantom lines in FIG. 5A where it is an engagement with the yieldably deformable central portion 28a of the cover. A continued downward movement of the stethoscope head in the direction of the arrow 41 of FIG. 5A will cause a deformation of the central portion of the cover in the manner shown in FIG. 5A. A further downward movement of the stethoscope head to the position shown in FIG. 5B will cause it to move through the generally key-hole-shaped opening 34 (see FIG. 3) and into the position shown in FIG. 5B of the drawings. As a stethoscope head moved downwardly through the keyhole shaped opening, the air-filled hollow tubes "T" of the stethoscope will pass through the segmented openings 23 and 24a formed in the base 20 and in the upstanding rim 24 respectively. As the stethoscope head moves downwardly, the elastomeric bead 30 will release from the rim portion of the base and, in the manner illustrated by the arrows 43 and FIG. 5A, will move into engagement with the peripheral portion "P" of the stethoscope head thereby removably securing the cover 28 to the stethoscope head and moving the flexible central membrane portion 28a of the cover into close engagement with the lower surface "S" of the stethoscope head. Once the cover is in position over the stethoscope head, the assemblage thus formed can be removed from the apparatus 12 in the manner illustrated in FIG. 5C. Following the examination of the patient, the cover assembly 26 can be conveniently removed from the stethoscope head and discarded into a suitable contaminated waste receptacle.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. In combination
   (a) a cover-positioning device for use in interconnecting a disposable stethoscope cover with a stethoscope head, said cover-positioning device comprising a base having a planar portion and an upstanding rim connected to said planar portion, said upstanding rim defining an opening for receiving the stethoscope head therethrough; and
   (b) a disposable stethoscope cover for removable attachment to a stethoscope head, said cover comprising a central portion having a peripheral portion and an elastomeric bead interconnected with said peripheral portion, said elastomeric bead being removably receivable over said upstanding rim of said cover-positioning device.

2. The combination as defined in claim 1 in which said central portion of said disposable stethoscope cover comprises a thin, yieldably deformable membrane.

3. The combination as defined in claim 1 in which said upstanding rim of said base includes an open segment.

4. The combination as defined in claim 3 in which said planar portion of said base includes an open segment in alignment with said open segment of said upstanding rim of said base.

5. A stethoscope head covering apparatus comprising:
   (a) a plurality of cover-positioning devices, each cover-positioning device comprising a base having a generally planar portion and an upstanding rim connected to said generally planar portion, said upstanding rim defining an opening;
   (b) a cover assembly connected to each of said plurality of cover-positioning devices to form a plurality of cover dispensing units each said cover assembly comprising:
      (i) a disposable cover having a central portion and a peripheral portion; and
      (ii) an elastomeric bead connected to said peripheral portion of said cover, said elastomeric bead being removably connected to said upstanding rim of a selected one of said plurality of cover-positioning devices; and
   (c) a feed unit for sequentially dispensing said plurality of cover dispensing units, said feed unit comprising a housing having:
      (i) a base having a forward portion and a rearward portion, said forward portion having a generally key-hole-shaped opening formed therein;
      (ii) an upstanding tower connected to said rearward portion of said base for holding a plurality of stacked cover dispensing units, said upstanding tower having a slot formed therein proximate said base; and
      (iii) an ejector slide received within said slot of said upstanding tower for movement between a first retracted position and a second dispensing position for moving a selected one of said cover dispensing units over said generally key-hole-shaped opening formed in said base of said feed unit.

6. The apparatus as defined in claim 5 in which said central portion of said disposable stethoscope cover comprises a thin, yieldably deformable membrane.

7. The apparatus as defined in claim 5 in which said upstanding rim of said base includes an open segment.

8. The apparatus as defined in claim 7 in which said planar portion of said base includes an open segment in alignment with said open segment of said upstanding rim of said base.

9. A stethoscope head covering apparatus comprising:
   (a) a plurality of cover-positioning devices, each cover-positioning device comprising a base having a generally planar portion and an upstanding rim connected to said generally planar portion, said upstanding rim having an open segment;
   (b) a cover assembly connected to each of said plurality of cover-positioning devices to form a plurality of cover dispensing units, each said cover assembly comprising:
      (i) a disposable cover having a thin, yieldably deformable central portion and a peripheral portion; and
      (ii) an elastomeric bead connected to said peripheral portion of said cover, said elastomeric bead being removably connected to said upstanding rim of a selected one of said plurality of cover-positioning devices; and
   (c) a feed unit for sequentially dispensing said plurality of cover dispensing units, said feed unit comprising a housing having:
      (i) a base having a forward portion and a rearward portion, said forward portion having a generally key-hole-shaped opening formed therein;
      (ii) an upstanding tower connected to said rearward portion of said base, said tower having a dispensing chamber for holding a plurality of stacked cover dispensing units, said dispensing chamber of said tower having a slot formed therein proximate said base; and
      (iii) an ejector slide received within said slot of said dispensing chamber for movement between a first retracted position and a second dispensing position for moving a selected one of said cover dispensing units over said generally key-hole-shaped opening formed in said base of said dispenser.

10. The apparatus as defined in claim 9 in which said planar portion of said base includes an open segment in alignment with said open segment of said upstanding rim of said base.

* * * * *